(12) United States Patent
Worster et al.

(10) Patent No.: US 11,771,344 B2
(45) Date of Patent: Oct. 3, 2023

(54) SENSOR MEASUREMENT FOR MOTOR CONTROL

(71) Applicant: Medtronic Navigation, Inc., Louisville, CO (US)

(72) Inventors: Katy L. Worster, Broomfield, CO (US); Victor D. Snyder, Erie, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 381 days.

(21) Appl. No.: 17/081,651

(22) Filed: Oct. 27, 2020

(65) Prior Publication Data

US 2022/0125340 A1    Apr. 28, 2022

(51) Int. Cl.
| | |
|---|---|
| *A61B 5/11* | (2006.01) |
| *A61B 5/00* | (2006.01) |
| *A61N 1/36* | (2006.01) |

(52) U.S. Cl.
CPC .......... *A61B 5/1124* (2013.01); *A61B 5/1101* (2013.01); *A61B 5/1126* (2013.01); *A61B 5/4082* (2013.01); *A61B 5/4836* (2013.01); *A61B 5/6826* (2013.01); *A61B 5/7282* (2013.01); *A61B 5/742* (2013.01); *A61B 5/7475* (2013.01); *A61N 1/36003* (2013.01); *A61B 2562/0223* (2013.01)

(58) Field of Classification Search
CPC ................ A61B 5/1124; A61B 5/6826; A61B 2562/0223; A61B 5/4082; A61B 5/1125; A61B 5/1101; A61B 5/6825; A61B 5/1114; A61B 2505/09; A61N 1/36003; A61N 1/36067
USPC ....................................................... 600/595
See application file for complete search history.

(56) References Cited

U.S. PATENT DOCUMENTS

| | | |
|---|---|---|
| 5,778,885 A | 7/1998 | Doyama et al. |
| 7,419,473 B2 | 9/2008 | Kandor et al. |
| 7,972,285 B2 * | 7/2011 | Miyashita ............ A61B 5/6838 600/595 |
| 9,877,847 B2 | 1/2018 | Bettenga |
| 10,231,665 B2 | 3/2019 | Rahimi et al. |
| 2006/0245627 A1 | 11/2006 | Nagamune |
| 2007/0038154 A1 * | 2/2007 | Kandori ............... A61B 5/1125 600/595 |

(Continued)

FOREIGN PATENT DOCUMENTS

WO    2018063920 A1    4/2018

OTHER PUBLICATIONS

Dipietro, L., Sabatini, A. M., & Dario, P. (2003). Evaluation of an instrumented glove for hand-movement acquisition. Journal of rehabilitation research and development, 40(2), 179-190. (Year: 2003).*

(Continued)

*Primary Examiner* — Daniel L Cerioni
*Assistant Examiner* — Jonathan E. Cooper
(74) *Attorney, Agent, or Firm* — Shumaker & Sieffert, P.A.

(57) ABSTRACT

An example method includes, determining, based on data received from a plurality of sensors that are each attached to a respective finger of a plurality of fingers of a hand of a patient, data that represents movements of one or more fingers of the plurality of fingers; and determining, based on the data that represents the movements of the one or more fingers, one or more objective indications of motor control of the patient.

9 Claims, 7 Drawing Sheets

(56) References Cited

U.S. PATENT DOCUMENTS

| | | | | |
|---|---|---|---|---|
| 2013/0060124 | A1* | 3/2013 | Zietsma | A61B 5/1101 600/407 |
| 2014/0296657 | A1 | 10/2014 | Izmirli et al. | |
| 2017/0164870 | A1 | 6/2017 | Byrd et al. | |
| 2018/0353253 | A1 | 12/2018 | Bowling | |
| 2019/0175057 | A1 | 6/2019 | Krimsky | |
| 2021/0228107 | A1* | 7/2021 | Perera | A61B 5/1101 |
| 2021/0402172 | A1* | 12/2021 | Ross | A61B 5/6847 |

OTHER PUBLICATIONS

Wu, J. H. (2020). Decoding finger movements with multichannel electroencephalography (Order No. 28001916). Available from ProQuest Dissertations and Theses Professional. (2443897342). (Year: 2020).*

Schaffelhofer et al., "A New Method of Accurate Hand-and Arm-Tracking for Small Primates," Journal of Neural Engineering vol. 9, No. 2, Mar. 15, 2012, 13 pp.

O'Suilleabhain et al., "Validation for Tremor Quantification of an Electromagnetic Tracking Device," Movement Disorders, vol. 16, No. 2, Mar. 8, 2001, pp. 265-271.

Parizi et el., "AuraRing: Precise Electromagnetic Finger Tracking," Proceedings of the ACM on Interactive, Mobile, Wearable and Ubiquitous Technologies, vol. 3, No. 4, Article 150, Dec. 2019, 28 pp.

YouTube, "Approach to the Exam for Parkinson's Disease," retrieved from https://www.youtube.com/watch?v=cxHpFWKIfGw&feature=youtu.be, Aug. 31, 2018, 1 pp.

"Neurosurgery Navigation StealthStation Surgical Navigation System," Medtronic, retrieved from https://www.medtronic.com/us-en/healthcare-professionals/products/neurological/surgical-navigation-systems/stealthstation/cranial-neurosurgery-navigation.html, on Oct. 21, 2020, 9 pp.

* cited by examiner

SENSOR MEASUREMENT FOR MOTOR CONTROL

TECHNICAL FIELD

The disclosure relates to devices and techniques for objective measurement of motor control.

BACKGROUND

Medical devices may be used to treat a variety of medical conditions including motor control disorders. Medical electrical stimulation devices, for example, may deliver electrical stimulation therapy to a patient via implanted electrodes. The electrical stimulation therapy delivered to a patient by the medical electrical stimulation device may be adjusted based on its ability to reduce symptoms in the patient. Alternatively or additionally, drug therapy or surgical procedures, such as laser ablation, may be used to treat motor control disorders.

SUMMARY

The present disclosure relates to techniques for objective measurement of motor control. During programming of a medical device that delivers treatment, such as an electrical stimulation device, a practitioner may adjust various stimulation parameters of the treatment delivery to a patient based on motor control abilities of the patient. For instance, based on motor control abilities of the patient, the practitioner may use a programmer device to adjust one or more of an electrode combination, amplitude, frequency, and pulse width of electrical stimulation therapy, such as deep brain stimulation (DBS) therapy, to reduce movement disorder symptoms.

A practitioner alternatively or additionally may evaluate the efficacy of a surgical procedure, or evaluate or adjust drug therapy, based on motor control abilities of the patient. As a further alternative, based on motor control abilities of the patient, a practitioner may form a diagnosis of a medical condition, such as a spinal pathology, e.g., cervical spondylotic myelopathy. On the basis of the diagnosis, the practitioner may recommend therapy and/or surgery.

The practitioner may assess movement disorder symptoms of the patient by observing motor control abilities of the patient. For instance, the practitioner may observe the patient performing, or attempting to perform, various movements. Specifically, a clinical assessment of bradykinesia in a patient with Parkinson's may include assessing tremor by observing the patient at rest while looking for tremors, especially in hands. The assessment may also include rapid, large-amplitude motions, such as tap thumb and forefinger, open and close fist, palm pronation/supination, and toe or heel tap. The practitioner may observe and subjectively assess decreases in amplitude and slowing as the patient performs such movements. However, using subjective observations of movements may result in inconsistent results, which may be undesirable.

In accordance with one or more techniques of this disclosure, a system may utilize finger or hand mounted sensors to objectively measure performance of movements by a patient. For instance, a practitioner may attach sensors to fingers of a hand of the patient and request that the patient attempt to perform certain movements with the fingers and/or the hand. While the patient performs the movements, a controller may process data received from the sensors to determine one or more objective indications of motor control of the patient. Some example objective indications include, but are not limited to, a magnitude of a tremor in the hand of the patient; a rate of tapping of a finger of the plurality of fingers; and an amplitude of tapping of the finger of the plurality of fingers.

The practitioner may adjust various parameters of a treatment to be delivered by a medical device, such as electrical stimulation, based on the objective indication of motor control. Alternatively or additionally, based on the objective indication of motor control, a practitioner may make adjustments to a drug therapy, e.g., modifying drug dosage or selection of a drug for delivery to the patient. In this way, the techniques of this disclosure enable adjustment of therapy delivery based on consistent results provided via objective measurement. As further alternatives, based on the objective indication of motor control, the practitioner may evaluate efficacy of drug therapy, evaluate results of a surgical procedure, such as laser ablation, or make a diagnosis of a medical condition such as a spinal pathology.

As one example, a method includes determining, based on data received from a plurality of sensors that are each attached to a respective finger of a plurality of fingers of a hand of a patient, data that represents movements of one or more fingers of the plurality of fingers; and determining, based on the data that represents the movements of the one or more fingers, one or more objective indications of motor control of the patient.

As another example, a system may include a plurality of sensors configured for attachment to respective fingers of a plurality of fingers of a hand of a patient; and a processing circuitry configured to: determine, based on data received from the plurality of sensors, data that represents movements of one or more fingers of the plurality of fingers; and determine, based on the data that represents the movements of the one or more fingers, one or more objective indications of motor control of the patient.

The details of one or more aspects of the disclosure are set forth in the accompanying drawings and the description below. Other features, objects, and advantages will be apparent from the description and drawings, and from the claims.

DETAILED DESCRIPTION

Figure 1:
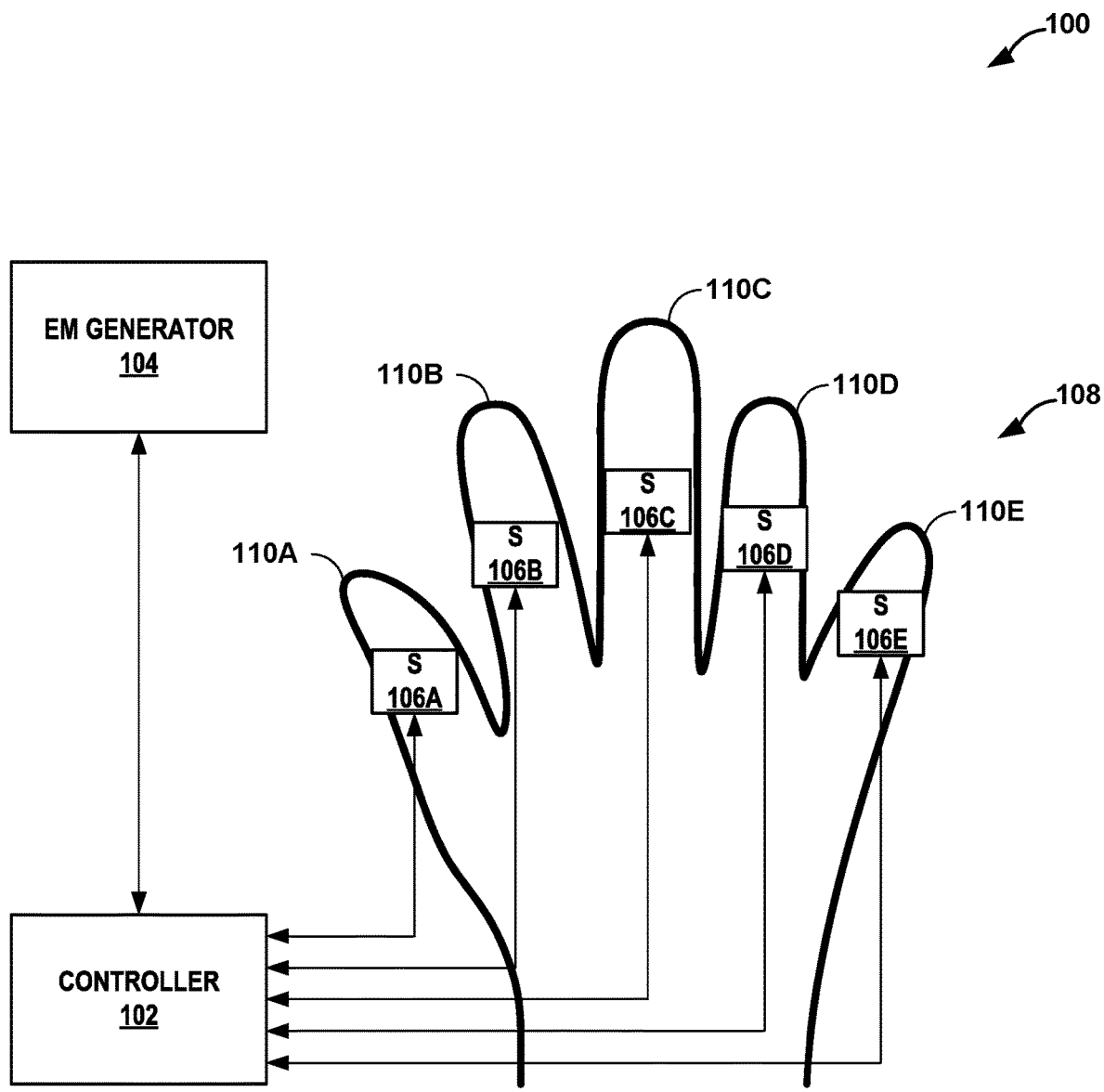
FIG. 1 is a conceptual diagram illustrating an example system for objectively accessing patient motor control, in accordance with one or more aspects of this disclosure.

FIG. 1 is a conceptual diagram illustrating an example system for objectively accessing patient motor control. As shown in FIG. 1, system 100 may include controller 102, electromagnetic (EM) generator 104, and sensors 106A-106E (collectively, "sensors 106").

Each respective sensor of sensors 106 may be configured to generate data that represents movement, position, and/or orientation of the respective sensor. As shown in FIG. 1, sensors 106 may be connected to controller 102 and may provide the generated data to controller 102. The connection between sensors 106 and controller 102 may be any suitable link, including wireless and wired links. Examples of sensors 106 include, but are not limited to, accelerometers, gyroscopes, electromagnetic (EM) coils, and the like.

As shown in FIG. 1, sensors of sensors 106 may be attached to various fingers 110A-110E (collectively, "fingers 110") of hand 108 of a patient. For instance, sensor 106A may be attached to finger 110A (e.g., a thumb), sensor 106B may be attached to finger 110B (e.g., an index finger), sensor 106C may be attached to finger 110C (e.g., a middle finger), sensor 106D may be attached to finger 110D (e.g., a ring finger), and sensor 106E may be attached to finger 110E (e.g., a pinkie finger). While shown in the example of FIG. 1 as including a respective sensor of sensor 106 attached to each of fingers 110, system 100 is not so limited. For instance, in other examples, one or more of sensors 106 may be omitted (e.g., sensors 106C-106E may be omitted) such that sensors of sensors 106 are only attached to a subset of fingers 110 (e.g., only attached to one or two fingers, such as fingers 110A and 110B).

In some examples, such as where sensors 106 are EM coils, system 100 may include EM generator 104, as shown in FIG. 1, which may be configured to generate an electromagnetic field. For instance, EM generator 104 may emit an electromagnetic field and the data generated by a sensor of sensors 106 may represent a position and/or an orientation of the sensor relative to the electromagnetic field emitted by EM generator 104. As such, EM generator 104 may define a coordinate system and each of sensors 106 may report its position and/or orientation in the defined coordinate system. For instance, 4 coils in a sensor of sensors 106 may report a measurement of the EM field emitted by EM generator 104, such measurements may represent a relative position of the sensor to EM generator 104. One specific example of sensors 106 and EM generator 104 is a combination of sensors and an EM generator similar to those provided by the StealthStation™ EM Surgical Navigation System, including the AxiEM electromagnetic tracking system, produced by Medtronic Inc.

Controller 102 may perform one or more operations to determine objective indications of motor control of a patient. For instance, controller 102 may determine, based on data received from a plurality of sensors 106, data that represents movements of one or more of fingers 110. Controller 102 may determine, based on the data that represents the movements of the one or more fingers, one or more objective indications of motor control of the patient. Some example objective indications of motor control include, but are not necessarily limited to, a magnitude of a tremor in hand 108, a rate of tapping of a finger of fingers 106, and an amplitude of tapping of the finger of fingers 106.

In some examples, controller 102 may determine the objective indications of motor control for one hand or each of both hands of the patient. For instance, using one or more sensors 106, where hand 108 is a first hand of the patient, controller 102 may determine a magnitude of a tremor in hand 108, a rate of tapping of a finger of fingers, an amplitude of tapping of the finger of fingers, a magnitude of a tremor in a second hand of the patient, a rate of tapping of a finger of the second hand, and/or an amplitude of tapping of the finger of the second hand. In some examples, two sets of sensors 106 may be used to determine the objective motion indications for both hands. In other examples, one or more of sensors 106 may be moved from the first hand to the second hand, such that the hands are evaluated separately at different times using the same shared set of sensors. In some examples, controller 102 may only determine the objective indications of motor control for a single hand of the patient (e.g., and not determine the objective indications for the other hand).

Controller 102 may output an indication of the determined one or more objective indications. For instance, controller 102 may output, for display at a display device, a graphical user interface (GUI) that includes a graphical and/or textual representation of the determined one or more objective indications. As one example, controller 102 may output a GUI that includes one or more of the magnitude of the tremor in hand 108, the rate of tapping of the finger of fingers 106, and the amplitude of tapping of the finger of fingers 106.

Controller 102 may adjust or be used to adjust, based on the one or more objective indications of motor control of the patient, one or more parameters of a therapy to be delivered to the patient via a medical device. For instance, controller 102 may output the objective indications to a programmer device that is configured to control operation of the medical device. As one example, controller 102 may automatically adjust one or more parameters of an electrical stimulation therapy to be delivered to the patient to treat a movement disorder. The one or more parameters of the electrical stimulation therapy include, but are not limited to, an amplitude, a pulse width, a dose, a frequency, and the like. As another example, controller 102 may automatically adjust one or more parameters of a drug delivery device that delivers a drug to the patient.

Controller 102 may be a hand-held computing device with a display viewable by the practitioner (e.g., a clinician, nurse, technician or other medical personnel) or another user and an interface for providing input to controller 102 (i.e., a user input mechanism). In other examples, controller 102 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate in the manner described herein.

Figure 2:
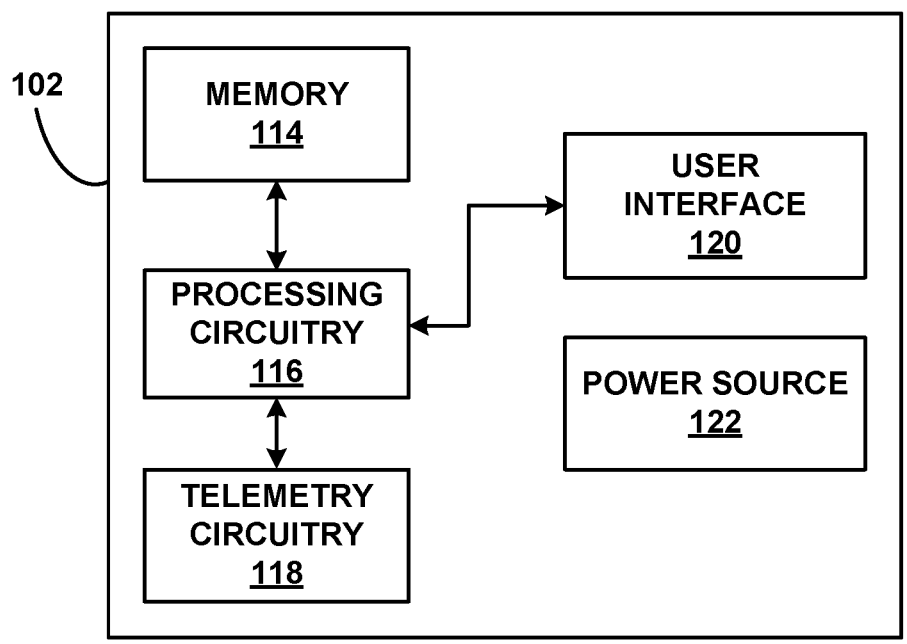
FIG. 2 is a conceptual diagram illustrating the example controller shown in FIG. 1.

FIG. 2 is a functional block diagram illustrating components of controller 102. In the example shown in FIG. 2, controller 102 includes memory 114, processing circuitry 116, telemetry circuitry 118, user interface 120, and power source 122. Processing circuitry 116 may include any one or more microprocessors, controllers, digital signal processors (DSPs), application specific integrated circuits (ASICs), field-programmable gate arrays (FPGAs), or discrete logic circuitry. The functions attributed to processors described herein, including processing circuitry 116, may be provided by processing circuitry of a hardware device, e.g., as supported by software and/or firmware.

Memory 114 may include any volatile or non-volatile media, such as a random access memory (RAM), read only memory (ROM), non-volatile RAM (NVRAM), electrically erasable programmable ROM (EEPROM), flash memory, and the like. Memory 114 may store computer-readable instructions that, when executed by processing circuitry 116, cause controller 102 to perform various functions described herein. Memory 114 may be considered, in some examples, a non-transitory computer-readable data storage medium comprising instructions that cause one or more processors, such as, e.g., processing circuitry 116, to implement one or more of the example techniques described in this disclosure. The term "non-transitory" may indicate that the data storage medium is not embodied in a carrier wave or a propagated signal. However, the term "non-transitory" should not be interpreted to mean that memory 114 is non-movable. As one example, memory 114 may be removed from controller 102, and moved to another device. In certain examples, a non-transitory storage medium may store data that can, over time, change (e.g., in RAM).

Telemetry circuitry 118 may support wired or wireless communication between controller 102 and an external device or another computing device under the control of processing circuitry 116. Telemetry circuitry 118 in controller 102, as well as telemetry modules in other devices and systems described herein, may accomplish communication by radiofrequency (RF) communication techniques. In addition, telemetry circuitry 118 may communicate with another device via proximal inductive interaction of controller 102 with the other device. Accordingly, telemetry circuitry 118 may send or receive information to the other device on a continuous basis, at periodic intervals, or upon request from processing circuitry 116 or the other device. For instance, processing circuitry 116 may periodically trigger telemetry circuitry 118 to receive data from sensors, such as sensors 106 of FIG. 1.

User interface 120 may include one or more components configured to present information to a user of controller 102 and/or receive user input from the user. User interface 120 may include one or more of: a display (which may or may not be a touchscreen), a speaker, a microphone, a camera, and the like.

Power source 122 delivers operating power to various components of controller 102. Power source 122 may include a connection to an external power source and/or a rechargeable or non-rechargeable battery.

In operation and in accordance with one or more techniques of this disclosure, controller 102 may determine, based on data that represents movements of one or more fingers of a patient, one or more objective indications of motor control of the patient, e.g., as received from one or more sensors 106. For instance, while one or more sensors (e.g., sensors 106 of FIG. 1) are attached to the one or more fingers of the patient, the patient may perform one or more predefined movements. Examples of such predefined movements include, but are not limited to, attempting to hold their hand steady and/or tapping a particular finger. As discussed above, examples of the objective indications include a magnitude of a tremor in the hand of the patient (e.g., a magnitude of an involuntary movement in the hand), a rate of tapping of a finger of the plurality of fingers (e.g., as the patient is intentionally tapping the finger), and/or an amplitude of tapping of the finger of the plurality of fingers (e.g., as the patient is intentionally tapping the finger).

Figure 3:
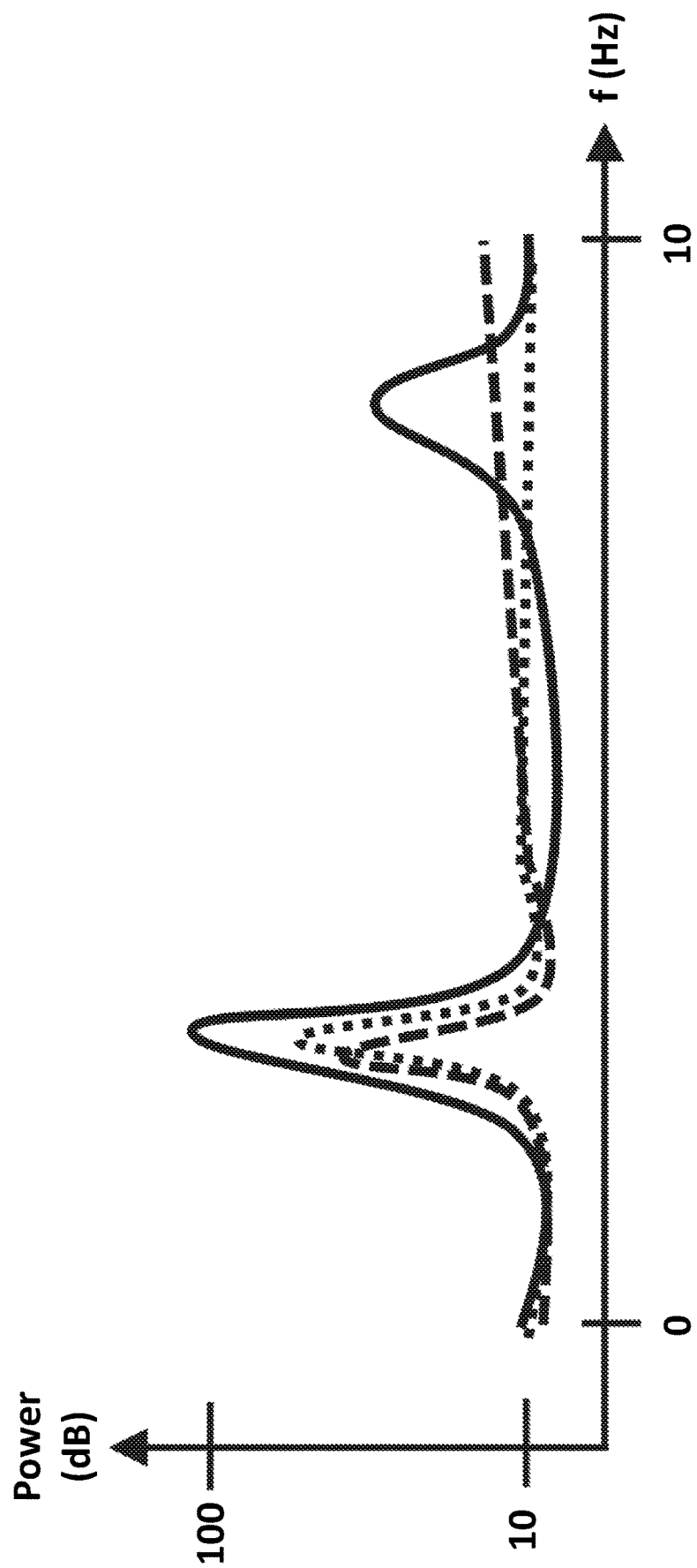
FIG. 3 is a graph illustrating an example power spectral density for objective assessment of tremor, in accordance with one or more aspects of this disclosure.

To determine the magnitude of the tremor, controller 102 may receive (e.g., via telemetry circuitry 118), while the patient is performing a movement, data from the sensors. As discussed above, the data from a particular sensor may represent one or more degrees of freedom (e.g., up to three degrees of positional freedom and/or up to three degrees of orientational freedom) of a finger to-which the particular sensor is attached. Processing circuitry 116 may process the received data to determine a power spectral density of the received data (e.g., that represents the movements of the one or more fingers of the plurality of fingers). For instance, let the received data be $r_i(t)$ $\forall i$ (where $r_1$ is the data received from a sensor on finger i, each sample of the data including at least a position of the sensor, which may be represented as $x_i, y_i, z_i$). Processing circuitry 116 may compute the power spectra of $(x_i, y_i, z_i)$ of a direction of largest variation (as found by principal component analysis (PCA)). FIG. 3 is a graph illustrating an example of power spectral density of data received from sensors 106, with different traces representing data from different sensors on different fingers. In FIG. 3, the vertical axis may represent power and the horizontal axis may represent frequency. Processing circuitry 116 may identify peaks in the determined power spectral density, the height of the identified peaks representing the magnitude of the tremor (e.g., and the locations of the identified peaks gives the frequency of the tremor). A magnitude of tremor above a threshold, e.g., as represented by the peaks, may indicate poor motor control or the presence of movement disorder symptoms.

Figure 4:
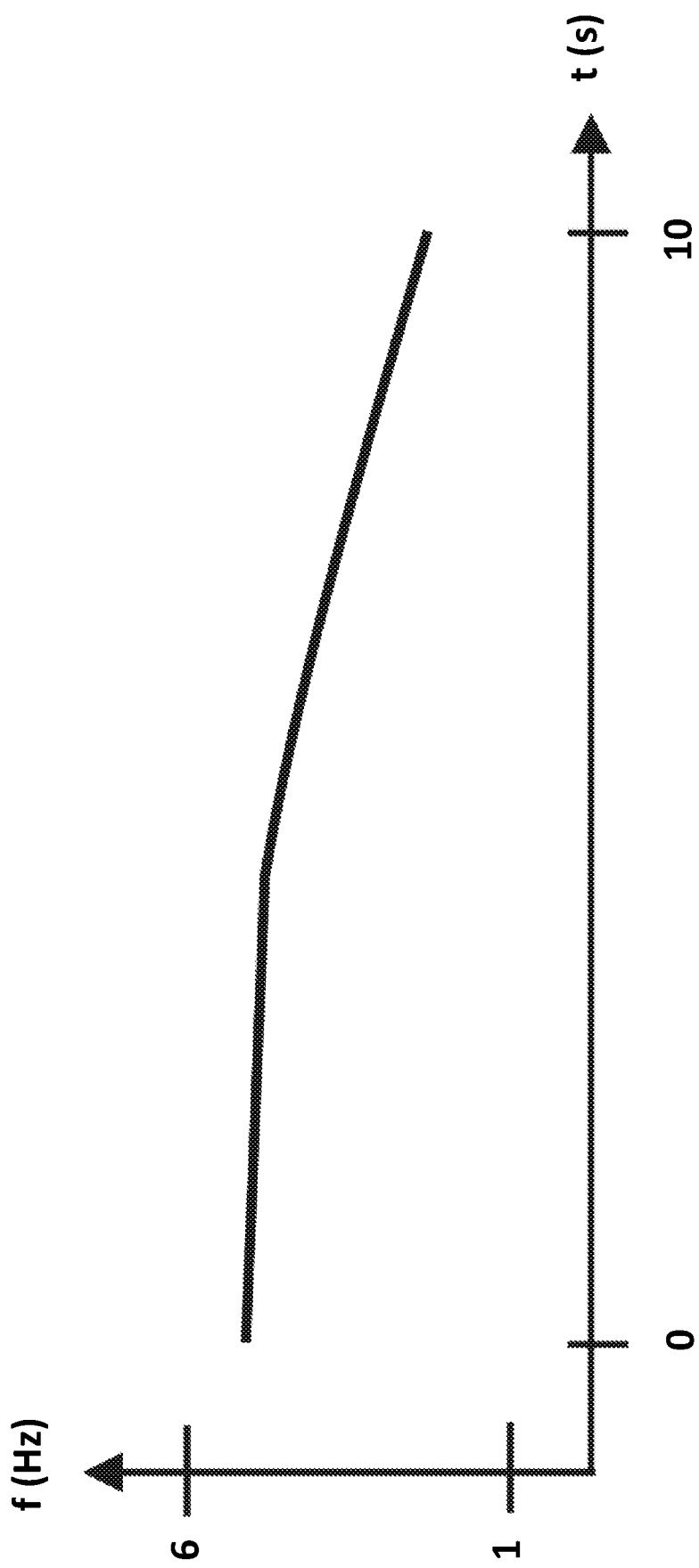
FIG. 4 is a graph illustrating an example spectrogram for object assessment of finger tapping rate, in accordance with one or more aspects of this disclosure.

To determine the rate of tapping of the finger, controller 102 may determine, as a function of time and based on the data that represents the movements of the one or more fingers of the plurality of fingers, a frequency of movement of the finger. For instance, let the received data be position $r_i(t)$, controller 102 may determine displacement $d(t)=|r_1(t)-r_2(t)|$, $r_1(t)$ may represent the position of a first finger with respect to time and $r_2(t)$ may represent the position of a second finger with respect to time. Controller 102 may determine a spectrogram (e.g., a relationship between frequency and time) of the determined relative displacement (e.g., determine a spectrogram of d(t)), the spectrogram representing the rate of tapping). FIG. 4 is a graph illustrating an example of such a spectrogram. In FIG. 4, the vertical axis may represent frequency and the horizontal axis may represent time. Controller 102 may analyze the spectrogram for decreasing frequency, which may indicate poor motor control or the presence of movement disorder symptoms.

Figure 5:
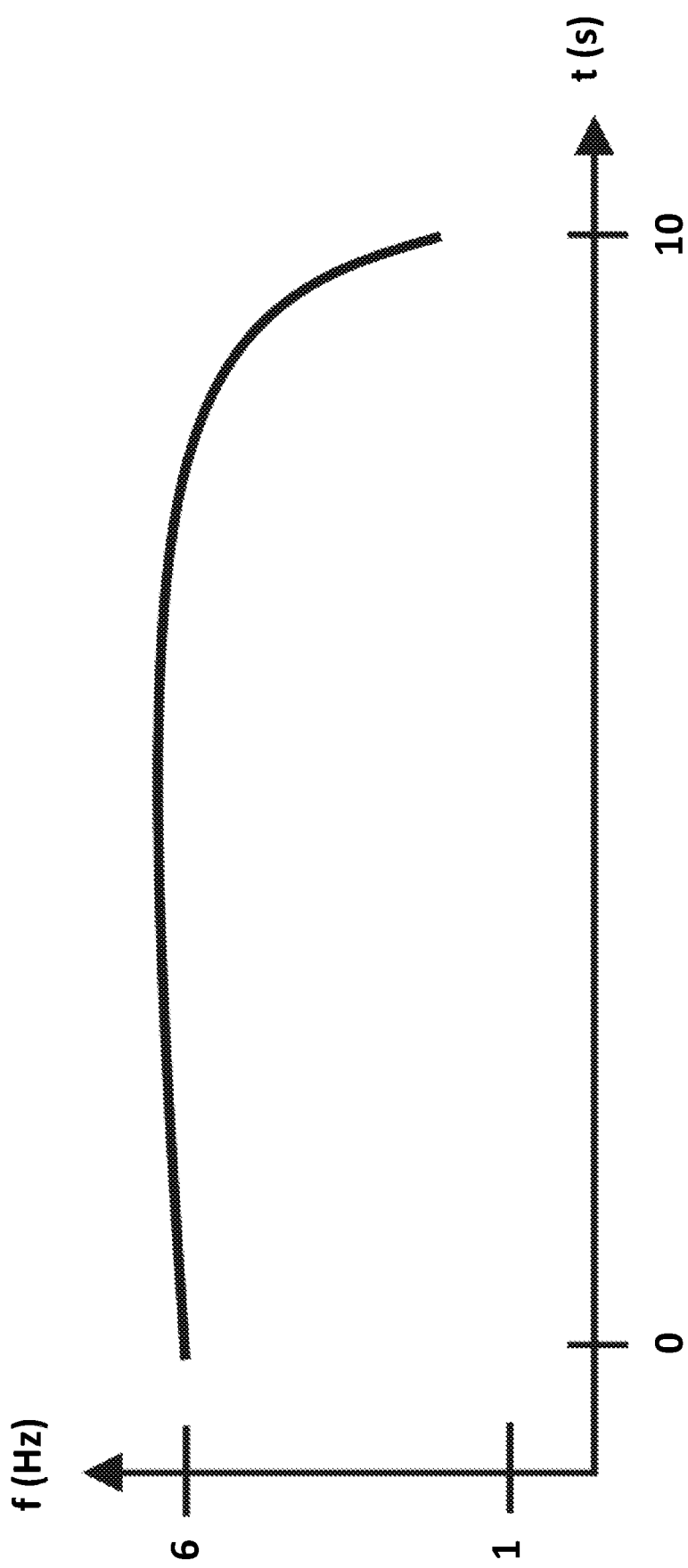
FIG. 5 is a graph illustrating an example displacement for objective assessment of finger tapping amplitude, in accordance with one or more aspects of this disclosure.

To determine the amplitude of tapping of the finger, controller 102 may determine, as a function of time and based on the data that represents the movements of the one or more fingers of the plurality of fingers, a relative displacement of the finger of the plurality of fingers to another finger of the plurality of fingers. For instance, letting the received data be position $r_i(t)$, controller 102 may determine displacement $d(t)=|r_1(t)-r_2(t)|$. Controller 102 may determine, based on a plurality of values of the determined relative displacement, respective maximum displacements of the finger during a plurality of respective time periods. For instance, controller 102 may compute D(t)=max d(t') for some window T. FIG. 5 is a graph illustrating an example of such maximum displacements over time. In FIG. 5, the vertical axis may represent displacement (e.g., amplitude) and the horizontal axis may represent time. Controller 102 may analyze the determined respective maximum displacements for decreasing amplitude (e.g., evaluate for decreasing D(t)), which may indicate poor motor control or the presence of movement disorder symptoms.

As discussed above, based on the determined one or more objective indications, controller 102 may adjust one or more parameters of a therapy to be delivered to the patient via a medical device. For instance, where one or more of the objective indications indicates poor motor control or the presence of movement disorder symptoms, controller 102 may adjust the one or more parameters in an attempt to improve motor control or reduce movement disorder symptoms. In some examples, controller 102 may re-determine the objective indications after adjusting the one or more parameters (e.g., to determine whether the adjustment was beneficial in improving motor control or reducing movement disorder symptoms). Controller 102 may repeat this process over one or more iterations until a desired state is achieved (e.g., driving one or more of a magnitude of tremor below a threshold magnitude, the magnitude of the tremor to a minimum level, a rate of finger tapping to hold steady, and/or a decrease in amplitude of displacement of tapping that is above a displacement threshold (e.g., no or minimal decrease in amplitude)). In subsequent iterations, controller 102 may determine the objective indications while therapy is being delivered to the patient (e.g., therapy adjusted based on previous iterations). The aforementioned iterative process can be performed fully automatically by controller 102 (e.g., controller 102 may interface with a therapy delivering device to adjust the one or more parameters), or may be partially automatic with input from a clinician (e.g., the clinician may review the results of an iteration before controller 102 begins a next iteration).

In some examples, in addition to or in-place of the aforementioned graphs, controller 102 may output one or more metrics or other scores that are determined based on the one or more objective indications. For instance, controller 102 may output a numerical value for each of the one or more objective indications (e.g., a numerical value for one or more of the magnitude of a tremor in the hand of the patient, the frequency of the tremor in the hand of the patient, the rate of tapping of a finger of the plurality of fingers, and/or the amplitude of tapping of the finger of the plurality of fingers. Additionally or alternatively, controller 102 may output a single score summarizing the one or more objective indications.

Figure 6:
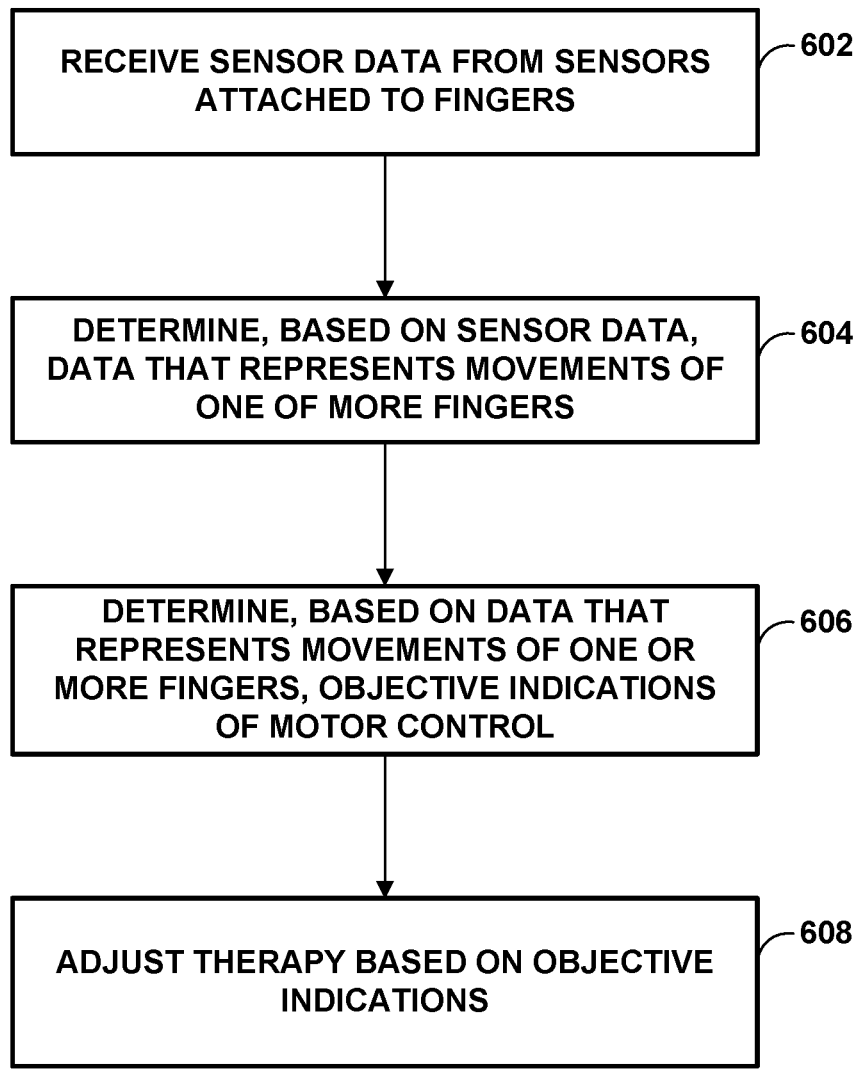
FIG. 6 is a flow diagram illustrating an example technique for objectively assessing patient motor control, in accordance with one or more aspects of this disclosure.

FIG. 6 is a flow diagram illustrating an example technique for objectively measuring indications of motor control, in accordance with one or more aspects of this disclosure. For ease of description, the example technique of FIG. 6 is described with regard to system 100 of FIG. 1. However, any suitable system including sensors and a controller may be employed to perform the example technique of FIG. 6.

As shown in FIG. 6, controller 102 of system 100 may receive sensor data from sensors attached to fingers (602). For instance, controller 102 may receive sensors data from one or more of sensors 106 that are respectively attached to fingers 110 of hand 108 of a patient. As discussed above, in some examples, the sensors may be EM sensors that provide data representing respective position and orientation with respect to an EM field generated by EM generator 104 of system 100.

Controller 102 may determine, based on the sensor data, data that represents movements of one or more fingers (604). For instance, controller 102 may determine, based on the data received from sensors 106, position and/or orientation (e.g., up to and including six degrees of freedom) of one or more of fingers 110.

Controller 102 may determine, based on the data that represents the movements of the one or more fingers, one or more objective indications of motor control of the patient (606). For instance, controller 102 may determine one or more of: a magnitude of a tremor in the hand of the patient; a rate of tapping of a finger of the plurality of fingers; and an amplitude of tapping of the finger of the plurality of fingers. In some examples, controller 102 may output a representation of the objective indications. For instance, controller 102 may output, for display at a display device, a graphical user interface (GUI) that includes the representation of the objective indications. In some examples, the representation may be in the form of graphs (e.g., similar to graphs of FIGS. 3-5). In some examples, the representation may be a numerical quantity for each objective indication. In some examples, the representation may be a numerical quantity determined based on a plurality of the objective indications.

Controller 102 may adjust, based on the objective indications, therapy to be delivered to the patient (608). For instance, controller 102 may adjust one or more parameters of an electrical stimulation therapy to be delivered to the patient to treat a movement disorder. In some examples, in addition to or alternative to adjusting the therapy, controller 102 may output an indication of the determined objective indications (e.g., output a GUI via user interface 120). A practitioner may adjust the therapy parameters based on the output from controller 102. In this way, the techniques of this disclosure enable adjustment of therapy based on objective (e.g., as opposed to subjective) measures of motor control.

Figure 7:
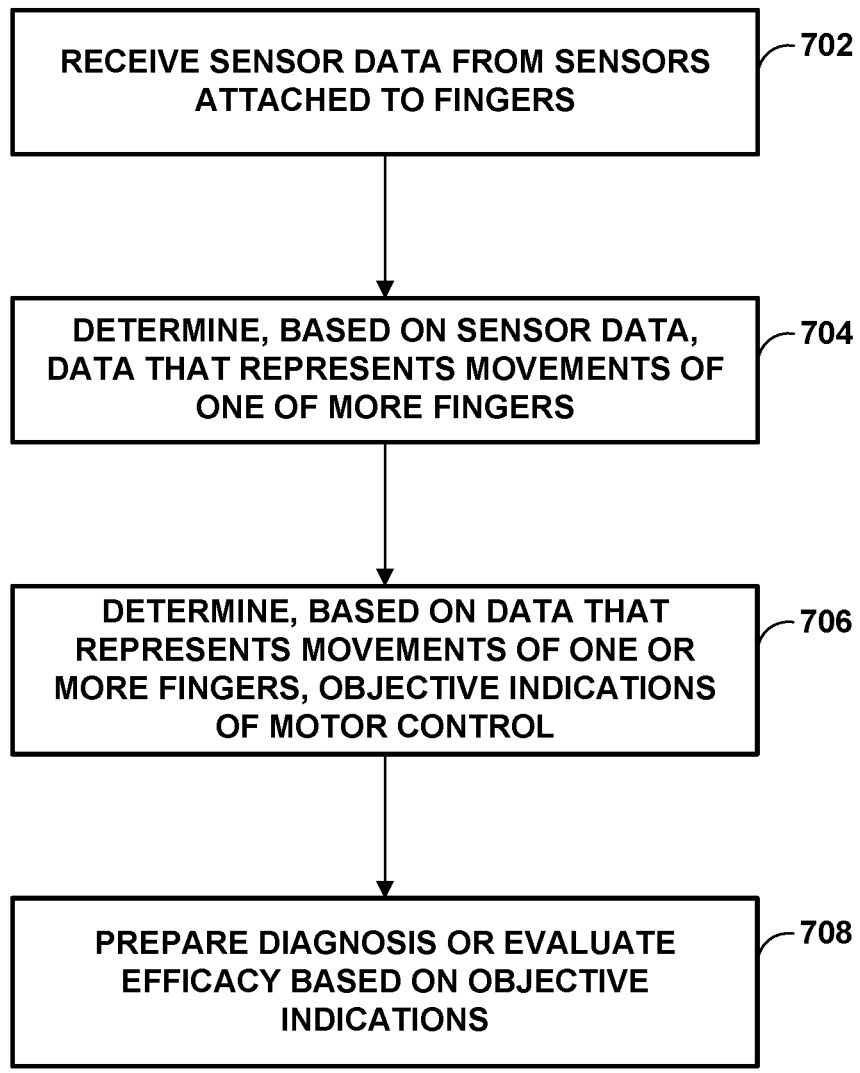
FIG. 7 is a flow diagram illustrating an example technique for objectively measuring indications of motor control, in accordance with one or more aspects of this disclosure.

FIG. 7 is a flow diagram illustrating an example technique for objectively measuring indications of motor control, in accordance with one or more aspects of this disclosure. For ease of description, the example technique of FIG. 7 is described with regard to system 100 of FIG. 1. However, any suitable system including sensors and a controller may be employed to perform the example technique of FIG. 7. Operations 702-706 of FIG. 7 may be considered to be examples of operations 602-606 of FIG. 6.

In some examples, in addition to or alternative to adjusting therapy (608), controller 102 may prepare a diagnosis or evaluate efficacy based on the objective indications (708). As one example, controller 102 may determine the objective indications during a time period in which the patient is being treated, the objective indications thus providing a measure of efficacy of the treatment. As another example, controller 102 may determine, based on the objective indications, whether the patient warrants a diagnosis of spondylotic myelopathy. By basing such a diagnosis on objective measures, delayed diagnosis may be avoided. This may be desirable as delayed diagnosis (with delayed treatment such as surgery) can have lasting or permanent detrimental effects.

The following numbered examples may illustrate one or more aspects of this disclosure:

Example 1. A method comprising: determining, based on data received from a plurality of sensors that are each attached to a respective finger of a plurality of fingers of a hand of a patient, data that represents movements of one or more fingers of the plurality of fingers; and determining, based on the data that represents the movements of the one or more fingers, one or more objective indications of motor control of the patient.

Example 2. The method of example 1, wherein the plurality of sensors each comprise an electromagnetic (EM) sensor that outputs data representing a relationship of the sensor to an EM field generated by an EM generator in proximity to the patient.

Example 3. The method of example 2, wherein the data that represents the movements of the one or more fingers comprises position data.

Example 4. The method of any of examples 1-3, wherein determining the one or more objective indications of motor control comprises one or more of: determining a magnitude of a tremor in the hand of the patient; determining a frequency of the tremor in the hand of the patient; determining a rate of tapping of a finger of the plurality of fingers; and determining an amplitude of tapping of the finger of the plurality of fingers.

Example 5. The method of example 4, wherein determining the magnitude of the tremor comprises: determining a power spectral density of the data that represents the movements of the one or more fingers of the plurality of fingers; and identifying peaks in the determined power spectral density.

Example 6. The method of any of examples 4-5, wherein determining the rate of tapping comprises: determining, as a function of time and based on the data that represents the movements of the one or more fingers of the plurality of fingers, a relative displacement of the finger of the plurality of fingers to another finger of the plurality of fingers; and determining a spectrogram of the determined relative displacement.

Example 7. The method of any of examples 4-6, wherein determining the amplitude of tapping comprises: determining, as a function of time and based on the data that represents the movements of the one or more fingers of the plurality of fingers, a relative displacement of the finger of the plurality of fingers to another finger of the plurality of fingers; and determining, based on a plurality of values of the determined relative displacement, respective maximum displacements of the finger during a plurality of respective time periods.

Example 8. The method of any of examples 1-7, further comprising: adjusting, based on the one or more objective indications of motor control of the patient, one or more parameters of a therapy to be delivered to the patient via a medical device.

Example 9. The method of example 8, wherein adjusting the one or more parameters of therapy comprises adjusting one or more parameters of an electrical stimulation therapy to be delivered to the patient to treat a movement disorder.

Example 10. The method of any of examples 1-9, further comprising: displaying a graphical user interface (GUI) that includes the one or more objective indications of motor control of the patient.

Example 11. A system comprising: a plurality of sensors configured for attachment to respective fingers of a plurality of fingers of a hand of a patient; and a processing circuitry configured to: determine, based on data received from the plurality of sensors, data that represents movements of one or more fingers of the plurality of fingers; and determine, based on the data that represents the movements of the one or more fingers, one or more objective indications of motor control of the patient.

Example 12. The system of example 11, further comprising: an electromagnetic (EM) generator configured to generate an EM field, wherein the plurality of sensors each comprise an EM sensor that outputs data representing a relationship of the sensor to the EM field.

Example 13. The system of example 12, wherein the data that represents the movements of the one or more fingers comprises position data.

Example 14. The system of any of examples 11-13, wherein, to determine the one or more objective indications of motor control, the processing circuitry is configured to one or more of: determine a magnitude of a tremor in the hand of the patient; determine a frequency of the tremor in the hand of the patient; determine a rate of tapping of a finger of the plurality of fingers; and determine an amplitude of tapping of the finger of the plurality of fingers.

Example 15. The system of example 14, wherein, to determine the magnitude of the tremor, the processing circuitry is configured to: determine a power spectral density of the data that represents the movements of the one or more fingers of the plurality of fingers; and identify peaks in the determined power spectral density.

Example 16. The system of any of examples 14-15, wherein, to determine the rate of tapping, the processing circuitry is configured to: determine, as a function of time and based on the data that represents the movements of the one or more fingers of the plurality of fingers, a relative displacement of the finger of the plurality of fingers to another finger of the plurality of fingers; and determine a spectrogram of the determined relative displacement.

Example 17. The system of any of examples 14-15, wherein, to determine the amplitude of tapping the processing circuitry is configured to: determine, as a function of time and based on the data that represents the movements of the one or more fingers of the plurality of fingers, a relative displacement of the finger of the plurality of fingers to another finger of the plurality of fingers; and determine, based on a plurality of values of the determined relative displacement, respective maximum displacements of the finger during a plurality of respective time periods.

Example 18. The system of any of examples 11-17, wherein the processing circuitry is further configured to: adjust, based on the one or more objective indications of motor control of the patient, one or more parameters of a therapy to be delivered to the patient via a medical device.

Example 19. The system of example 18, wherein, to adjust the one or more parameters of therapy, the processing circuitry is configured to adjust one or more parameters of an electrical stimulation therapy to be delivered to the patient to treat a movement disorder.

Example 20. The system of any of examples 11-19, wherein the processing circuitry is further configured to: output, for display, a graphical user interface (GUI) that includes the one or more objective indications of motor control of the patient.

Example 21. A computer-readable storage medium storing instructions that, when executed, cause processing circuitry to perform the method of any of examples 1-10.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

As used herein, the term "circuitry" may refer to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

The invention claimed is:

1. A system comprising:
a plurality of sensors configured for attachment to respective fingers of a plurality of fingers of a hand of a patient; and
processing circuitry configured to:
   determine, based on data received from the plurality of sensors, data that represents movements of one or more fingers of the plurality of fingers;
   determine, based on the data that represents the movements of the one or more fingers, one or more objective indications of motor control of the patient, wherein, to determine the one or more objective indications of motor control, the processing circuitry is configured to determine a rate of tapping of a finger of the plurality of fingers, and wherein, to determine the rate of tapping, the processing circuitry is configured to:
      determine, as a function of time and based on the data that represents the movements of the one or more fingers of the plurality of fingers, a relative displacement of the finger of the plurality of fingers to another finger of the plurality of fingers; and
      determine a spectrogram of the determined relative displacement; and
   adjust, based on the one or more objective indications of motor control of the patient, one or more parameters of a therapy to be delivered to the patient via a medical device.

2. The system of claim 1, further comprising:
an electromagnetic (EM) generator configured to generate an EM field, wherein the plurality of sensors each comprise an EM sensor that outputs data representing a relationship of the sensor to the EM field.

3. The system of claim 2, wherein the data that represents the movements of the one or more fingers comprises position data.

4. The system of claim 1, wherein, to determine the one or more objective indications of motor control, the processing circuitry is further configured to one or more of:
determine a magnitude of a tremor in the hand of the patient;
determine a frequency of the tremor in the hand of the patient; and
determine an amplitude of tapping of the finger of the plurality of fingers.

5. The system of claim 4, wherein, to determine the magnitude of the tremor, the processing circuitry is configured to:
determine a power spectral density of the data that represents the movements of the one or more fingers of the plurality of fingers; and
identify peaks in the determined power spectral density.

6. The system of claim 4, wherein, to determine the amplitude of tapping the processing circuitry is configured to:
determine, as a function of time and based on the data that represents the movements of the one or more fingers of the plurality of fingers, a relative displacement of the finger of the plurality of fingers to another finger of the plurality of fingers; and
determine, based on a plurality of values of the determined relative displacement, respective maximum displacements of the finger during a plurality of respective time periods.

7. The system of claim 1, wherein, to adjust the one or more parameters of therapy, the processing circuitry is configured to adjust one or more parameters of an electrical stimulation therapy to be delivered to the patient to treat a movement disorder.

8. The system of claim 1, wherein the processing circuitry is further configured to:
output, for display, a graphical user interface (GUI) that includes the one or more objective indications of motor control of the patient.

9. A system comprising:
a plurality of sensors configured for attachment to respective fingers of a plurality of fingers of a hand of a patient; and
processing circuitry configured to:
   determine, based on data received from the plurality of sensors, data that represents movements of one or more fingers of the plurality of fingers;
   determine, based on the data that represents the movements of the one or more fingers, one or more objective indications of motor control of the patient, wherein, to determine the one or more objective indications of motor control, the processing circuitry is configured to determine an amplitude of tapping of a finger of the plurality of fingers, and wherein, to determine the amplitude of tapping, the processing circuitry is configured to:
      determine, as a function of time and based on the data that represents the movements of the one or more fingers of the plurality of fingers, a relative displacement of the finger of the plurality of fingers to another finger of the plurality of fingers; and
      determine, based on a plurality of values of the determined relative displacement, respective maximum displacements of the finger during a plurality of respective time periods; and adjust, based on the one or more objective indications of motor control of the patient, one or more parameters of a therapy to be delivered to the patient via a medical device.

\* \* \* \* \*